(12) United States Patent
Grgurevic et al.

(10) Patent No.: US 8,182,998 B2
(45) Date of Patent: May 22, 2012

(54) BLOOD BIOMARKERS FOR BONE FRACTURE AND CARTILAGE INJURY

(75) Inventors: Lovorka Grgurevic, Zagreb (HR); Boris Macek, Zagreb (HR); Slobodan Vukicevic, Zagreb (HR)

(73) Assignee: Genera Istrazivanja d.o.o., Kalinovica (HR)

( * ) Notice: Subject to any disclaimer, the term of this patent is extended or adjusted under 35 U.S.C. 154(b) by 34 days.

(21) Appl. No.: 12/451,100

(22) PCT Filed: Apr. 28, 2008

(86) PCT No.: PCT/US2008/005463
§ 371 (c)(1),
(2), (4) Date: Oct. 23, 2009

(87) PCT Pub. No.: WO2008/134054
PCT Pub. Date: Nov. 6, 2008

(65) Prior Publication Data
US 2010/0112721 A1    May 6, 2010

Related U.S. Application Data

(60) Provisional application No. 60/926,316, filed on Apr. 26, 2007.

(51) Int. Cl.
*G01N 33/53* (2006.01)
*C07K 14/435* (2006.01)
*C07K 14/705* (2006.01)
*C07K 14/71* (2006.01)

(52) U.S. Cl. ............................ 435/7.1; 435/7.2; 530/350

(58) Field of Classification Search .................. None
See application file for complete search history.

(56) References Cited

U.S. PATENT DOCUMENTS

| | | | |
|---|---|---|---|
| 2002/0058614 A1 | 5/2002 | Filvaroff et al. |
| 2003/0015208 A1 | 1/2003 | Lang et al. |

FOREIGN PATENT DOCUMENTS

| | | |
|---|---|---|
| WO | WO 02/33085 A2 | 4/2002 |
| WO | WO 02/059308 A2 | 8/2002 |
| WO | WO 2006/023412 A2 | 3/2006 |
| WO | WO 2008/011193 A2 | 1/2008 |

OTHER PUBLICATIONS

Anderson et al., "The Human Plasma Proteome: History, Character, and Diagnostic Prospects", *Mol. Cell. Proteomics*, 1: 845-867 (2002).
Barnes et al., "Growth Factor Regulation of Fracture Repair", *J. Bone Miner. Res.*, 14: 1805-1815 (1999).
Benz et al.,"Molecular analysis of expansion, differentiation, and growth factor treatment of human chondrocytes identifies differentiation markers and growth-related genes", *Biochemical and Biophysical Research Communications*, 293: 284-292 (abstract) (2002).
Dong et al., "The type III TGF-β receptor suppresses breast cancer progression", *J. Clin. Invest.*, 117: 206-217 (2007).
Grgurevic et al., "Urine release of systemically administered bone morphogenetic protein hybrid molecule", *J. Nephrol.*, 20: 311-319 (2007).
Holliger et al., "Diabodies": Small bivalent and bispecific antibody fragments, *Proc. Natl. Acad. Sci. USA*, 90: 6444-6448 (1993).
Holliger et al.," Diabodies: small bispecific antibody fragments", *Cancer Immunol. Immunother.*, 45: 128-130 (1997).
Kriangkum et al., "Bispecific and bifunctional single chain recombinant antibodies", *Biomol. Eng.*, 18: 31-40 (2001).
Massague, J.,"TGF-β Signal Transduction", *Ann. Rev. Biochem.*, 67: 753-791 (1998).
Miller et al., "Design, Construction, and in Vitro Analyses of Multivalent Antibodies", *J. Immunol.*, 170: 4854-4861 (2003).
Milstein et al., "Hybrid hybridomas and their use in immunohistochemistry", *Nature*, 305: 537-540 (1983).
Olsen et al., "Parts per Million Mass Accuracy on an Orbitrap Mass Spectrometer via Lock Mass Injection into a C-trap", *Mol. Cell. Proteomics*, 4: 2010-2021 (2005).
Steck et al., "Chondrocyte secreted CRTAC1: A glycosylated extracellular matrix molecule of human_articular cartilage", *Matrix Biol.*, 26: 30-41 (2007).
Turley et al., "The Type III Transforming Growth Factor-β Receptor as a Novel Tumor Suppressor Gene in Prostate Cancer", *Cancer Res.*, 67: 1090-1098 (2007).
Wu et al., "Tumor localization of anti-CEA single-chain Fvs: improved targeting by non-covalent dimmers", *Immunotech.*, 2: 21-36 (1996).
Wu et al., "Simultaneous targeting of multiple disease mediators by a dual-variable-domain immunoglobulin", *Nature Biotechnology*, 1-8 (2007).
He et al., "The human plasma proteome: Analysis of Chinese serum using shotgun strategy," Proteomics, 5: 3442-3453 (2005).
Henle et al., "Matrix metalloproteinases and failed fracture healing," Bone, 37: 791-798 (2005).
Jones A.R.C., et al., "Binding and localization of recombinant lubricin to articular cartilage surfaces," J. Orthop. Res., 25: 283-292 (2007) [advanced online publication date Nov. 14, 2006].
Rhee et al., "The secreted glycoprotein lubricin protects cartilage surfaces and inhibits synovial cell overgrowth," J. Clin. Invest, 115: 622-631 (2005).
Schmidt et al., "Synthesis of proteoglycan 4 by chondrocyte subpopulation in cartilage explants, monolayer cultures and resurfaced cartilage cultures," Arthritis Rheum., 50: 2849-2857 (2004).
Schumacher et al., "Proteoglycan 4 (PRG4) synthesis and immunolocalization in bovine meniscus," J. Orthop. Res., 23: 562-568 (2005).
Simic and Vukicevic, "Bone morphogenetic proteins: from developmental signals to tissue regeneration. Conference on bone morphogenetic proteins." EMBO Rep., 8: 327-331 (2007).

(Continued)

*Primary Examiner* — Christine J Saoud
*Assistant Examiner* — Jon M Lockard
(74) *Attorney, Agent, or Firm* — Thomas R. Berka; Leon R. Yankwich; Yankwich & Associates, P.C.

(57) ABSTRACT

Blood biomarkers are described for use in methods and compositions to determine whether an individual has sustained a bone fracture or a cartilage injury.

9 Claims, 2 Drawing Sheets

OTHER PUBLICATIONS

Grgurevic et al., "Detection of bone and cartilage-related proteins in plasma of patients with a bone fracture using liquid chromatography-mass spectrometry," International Orthopaedics, 31(6): 743-751 (2007).

Grgurevic et al., "Novel biomarkers in the plasma of patients with a bone fracture," Calcified Tissue International, 82(Suppl. 1): S122-S123 (Apr. 11, 2008) (XP 002588455).

Extended European Search Report issued Jul. 8, 2010, in counterpart application EP 08 743 369.4.

International Search Report issued Sep. 25, 2008, in international application No. PCT/US08/05463.

Written Opinion issued Sep. 25, 2008, in international application No. PCT/US08/05463.

International Preliminary Report on Patentability issued Oct. 27, 2009, in international application No. PCT/US08/05463.

Andres et al., "Binding of Two Growth Factor Families to Separate Domains of the Proteoglycan Betaglycan," J. Biol. Chem., 267: 5927-5930 (1992).

Andres et al., "Membrane-anchored and Soluble Forms of Betaglycan, a Polymorphic Proteoglycan that Binds Transforming Growth Factor-β," J. Cell Biol., 109: 3137-3145 (1989).

López-Casillas et al., "Betaglycan Presents Ligand to the TGFβ Signaling Receptor," Cell, 73: 1435-1444 (1993).

López-Casillas et al., "Structure and Expression of the Membrane Proteoglycan Betaglycan, a Component of the TGF-β Receptor System," Cell, 67: 785-795 (1991).

Sharma et al., "Neutralization of TGF-β by Anti-TGF-β Antibody Attenuates Kidney Hypertrophy and the Enhanced Extracellular Matrix Gene Expression in STZ-Induced Diabetic Mice," Diabetes, 45: 522-530 (1996).

Straume et al., "Importance of Vascular Phenotype by Basic Fibroblast Growth Factor, and Influence of the Angiogenic Factors Basic Fibroblast Growth Factor/Fibroblast Growth Factor Receptor-1 and Ephrin-A1/EphA2 on Melanoma Progression," Am. J. Pathol., 160: 1009-1019 (2002).

BLOOD BIOMARKERS FOR BONE FRACTURE AND CARTILAGE INJURY

CROSS-REFERENCE TO RELATED APPLICATIONS

This application is a United States national stage filing under 35 USC §371 of international application No. PCT/US2008/005463, filed Apr. 28, 2008, designating the US, which claims priority to US Provisional Application No. 60/926,316, filed Apr. 26, 2007.

FIELD OF THE INVENTION

This invention is in the field of diagnosis of injuries. More specifically, the invention discloses means and methods for a rapid and accurate detection of bone and cartilage injury in a human patient and other mammals based on the release into the peripheral circulation of proteins involved with bone and cartilage repair.

BACKGROUND OF THE INVENTION

The blood of humans and other mammals is now known to be rich with a large amount of previously unstudied molecules that could reflect the ongoing physiologic state of various tissues. As blood flows through most of the tissues of the human body, the origins of plasma proteins may be diverse. The complex mixture of a blood plasma proteome from a healthy human individual is expected to comprise well known blood component proteins such as albumin and other known proteins in a relatively high abundance and various other proteins that originate from circulating blood cells.

Bone normally undergoes continuous turnover and remodeling comprising bone formation and bone resorption; two opposite and well balanced processes. A number of proteins related to this normal regenerative process may be found in the plasma and/or urine of healthy individuals in amounts that are generally correlated with a relative decrease or increase in bone turnover activity. See, e.g., Anderson et al., *Mol. Cell. Proteomics*, 1: 845-867 (2002). Following fracture, a large number of growth factors, cytokines, and their cognate receptors involved in bone repair are highly expressed at the fracture site in the first hours following injury. Skeletal tissues are the main source of such proteins, while some are released from associated inflammatory cells at the site of injury. See, e.g., Barnes et al., *J. Bone Miner. Res.*, 14: 1805-1815 (1999).

Injuries to bones and cartilage are routinely assessed and monitored using such well known standard methods such as X-rays, bone scans, and magnetic resonance imaging (MRI). However, such methods typically require transporting a patient to a location that contains the machinery necessary to carry out such analyses. Yet there are many situations in which it would be advantageous to be able to determine whether a patient has sustained a bone fracture and/or cartilage injury without the need or benefit of X-ray, bone scan, or MRI studies. In addition, injuries to bone and cartilage are not always evident by such methods. Accordingly, needs remain for additional means and methods to detect and assess bone and cartilage injuries in patients.

SUMMARY OF THE INVENTION

The invention described herein solves the above problems by providing a rapid and accurate method for detecting a bone fracture and cartilage injuries in a human individual using a sample of the individual's blood. The invention is based on the discoveries that transforming growth factor beta receptor III (TGFβrIII), which normally is not present in the blood of a healthy human individual, appears in the peripheral blood when a bone is fractured and that the level of cartilage acidic protein 1 (CRTAC-1) is significantly elevated in the peripheral blood of an individual that has an injury to cartilage. TGFβrIII and elevated levels of CRTAC-1 continue to be detected in the blood for a period of time for at least 24 weeks after time of injury. Moreover, the detection of TGFβrIII or of elevated levels of CRTAC-1 in the blood provides a diagnostic test for the presence of injury to bone or cartilage, respectively, that may be more sensitive than commonly employed methods, such as X-ray, bone scan, and magnetic resonance imaging (MRI), which require specialized instruments. Furthermore, methods described herein can be routinely carried out to monitor bone fracture or cartilage injury in a patient. The methods described herein may be readily carried out using any of a variety of formats.

A method described herein may be carried out on whole blood or a fraction thereof, such as plasma or serum. Preferably, the plasma portion of blood is used in the methods described herein.

In one embodiment, the invention provides a method of detecting a fracture in a bone of a human individual in which a sample of blood is obtained from the human individual and assayed for the presence of transforming growth factor beta receptor III (TGFβrIII), wherein the detection of TGFβrIII in the blood sample indicates that the individual has sustained a bone fracture.

Methods of detecting TGFβrIII and/or CRTAC-1 in a sample of blood obtained from an individual according to the invention may also be used to measure (quantitate) the level of TGFβrIII and/or CRTAC-1 present in the sample of blood and thereby in the blood of the individual.

Since TGFβrIII is known to play a role in enhancing TGF-β signal transduction in the process of bone formation (osteogenesis), the presence of TGFβrIII in a sample of blood obtained from an individual may also be used as an indication that the process of osteogenesis is stimulated in the individual. Likewise, because CRTAC-1 is a component in the process of cartilage formation (chondrogenesis), the determination that there is an elevated level or an increasing level of CRTAC-1 over time in one blood sample relative to another obtained from an individual may be used as an indication that the process of chondrogenesis is stimulated in the individual.

In addition to methods for detecting whether an individual has sustained an injury to bone or cartilage, the invention also provides methods that may be used to routinely monitor the time course of injury to bone or cartilage in an individual without the use of X-rays, bone scans, or MRI studies. Such methods are especially useful in monitoring individuals that may be at increased risk of bone fracture or cartilage injury, such as an individual afflicted with osteoarthritis, osteoporosis, or a genetic disease that impairs osteogenesis or chondrogenesis, such as osteogenesis imperfecta (OI, "brittle bone disease") in which the bones of an individual are unusually brittle and susceptible to fracture. Such methods may also be used in monitoring an individual who may be suspected of having a bone or cartilage injury but is incapable of effective communication, such as infants; speaking impaired individuals; stroke patients; and patients in an altered consciousness state (ACS), such as coma, near coma, persistent vegetative state, vegetative state, or minimally conscious state. Such methods may also find use in the forensic analysis of injuries to an individual.

In another embodiment, the invention provides a method for monitoring the state of a bone fracture in an individual comprising assaying for the level of transforming growth factor beta receptor III (TGFβrIII) in a first blood sample and in a second blood sample, wherein the second blood sample was obtained within two weeks, preferably one week, inclusive, after the first blood sample from the individual, and comparing the level of TGFβrIII in the first blood sample with that of the second blood sample. In a further embodiment, a significant increase in the level of TGFβrIII of greater than about 20% or more between the first (earlier obtained) blood sample and the second (later obtained) blood sample indicates that the individual has sustained a bone fracture that occurred within about 1 to about 2 weeks prior to the time of the second blood sample. In another embodiment, a decrease in the level of TGFβrIII of greater than about 10% or more between the first blood sample and the second blood sample indicates that the individual has sustained a bone fracture that occurred within about 2 to about 6 weeks prior to the time of the second blood sample. In yet another embodiment, where the level of TGFβrIII remains essentially steady, i.e., where the change in the level of TGFβrIII between the first and second blood sample is of about 6% or less, including no increase or decrease, this indicates that the individual has sustained a bone fracture but has sustained no new bone fracture for at least about 6 weeks (more preferably, within about 6 to about 24 weeks) prior to the time of the second blood sample.

In another embodiment, the invention provides a method of detecting a cartilage injury in a human individual in which a sample of blood is obtained from the individual and assayed to determine the level of cartilage acidic protein 1 (CRTAC-1) in the blood sample, wherein a level of CRTAC-1 in the blood sample that is significantly higher, that is, at least about 20% or more higher than the level previously determined in a sample of blood from the individual indicates that the individual has sustained a cartilage injury. Following a cartilage injury in an individual, the level of CRTAC-1 in a blood sample of the individual increases dramatically in the first weeks following the injury, rising by at least about 40% (including as much as about 50%, about 60%, about 70%, about 80%, about 90%, and about 100%) higher than the level of CRTAC-1 in a blood sample from the individual prior to or at the time of the cartilage injury, or in comparison to a level previously determined in a blood sample from the individual or to a reference level or range of concentration for CRTAC-1 as determined from a healthy population of individuals not suffering from a cartilage injury.

In another embodiment, the invention provides a method for monitoring the state of a cartilage injury in an individual comprising assaying for the level of cartilage acidic protein 1 (CRTAC-1) in a first blood sample and in a second blood sample, wherein the second blood sample was obtained from the individual within two weeks, preferably within a week, inclusive, of the first blood sample from the individual, and comparing the level of CRTAC-1 in the first blood sample with that in the second blood sample. In a further embodiment, an increase in the level of CRTAC-1 of about 20% or more, more preferably about 24% or more, between the first (earlier obtained) blood sample and the second (later obtained) blood sample indicates that the individual has sustained a cartilage injury that occurred within about 1 to about 2 weeks prior to the time of the second blood sample. In still a further embodiment, a decrease in the level of CRTAC-1 of about 4.5% or more between the first blood sample and the second blood sample indicates that the individual has sustained a cartilage injury that occurred within about 6 to about 10 weeks prior to the time of the second blood sample. In another embodiment, where the level of CRTAC-1 measured in the first and second blood sample remains essentially steady, i.e., where the change in the level of CRTAC-1 is less than 2% between the first blood sample and the second blood sample, including no increase or decrease, indicates that the individual is in a steady state and has sustained no new cartilage injury for at least about 10 weeks prior to the time of the second blood sample.

Preferably, in a method described herein, a blood sample is assayed using a binding partner that specifically binds TGR-βrIII or CRTAC-1 as its cognate binding partner (cognate ligand). Binding partners include binding proteins and aptamers. Binding proteins useful in the methods and compositions described herein include, but are not limited to, full-length immunoglobulin antibody molecules comprising four polypeptide chains, i.e., two heavy (H) chains and two light (L) chains, wherein each pair of heavy and light chains forms an antigen binding site. Other binding proteins useful in the methods and compositions described herein include any of a variety of recombinant antibody constructs that possess an antigen binding site, including without limitation, a functional antibody fragment, such a Fab, F(ab')$_2$, and Fv; a hybrid antibody, such as a chimeric or humanized antibody; a single chain antibody (scFv); a diabody; a dual-variable domain immunoglobulin molecule; and the like. Such antibody binding proteins are especially advantageous as they may be employed in any of a variety of immunoassay formats in which a blood sample of an individual is brought into contact with an antibody binding protein for TGFβrIII and/or an antibody binding protein for CRTAC-1 under conditions suitable for the formation of a binding complex formed between the binding protein and the binding partner, which complex can then be detected using any of a variety methods available in the art for detecting antibody/antigen immunocomplexes.

A binding partner that binds TGFβrIII or CRTAC-1 may also have a detectable label (tag) or other molecule that permits detection of a binding complex formed between the binding partner and TGFβrIII or CRTAC-1 in a method described herein. Such detectable labels and other molecules are well known in the art and include, without limitation, fluorescent labels, radiolabels, colorimetric molecules, affinity beads, and the like.

Formats used for immunoassays to detect antibody/antigen immunocomplexes may also be employed in the methods and compositions described herein. Such formats for detecting or measuring the level of TGFβrIII or CRTAC-1 in a sample of blood according to the invention include, but are not limited to, enzyme linked immunoadsorbent assay (ELISA), immunoprecipitations, immunoblotting, affinity chromatography, assay strips, dip sticks, and the like, wherein the blood sample is brought into contact with a binding protein for TGFβrIII or CRTAC-1 and the resulting binding complex detected.

In yet another embodiment, the invention provides a kit for detecting or measuring the level of TGFβrIII and/or CRTAC-1 in a sample of blood from an individual to determine if the individual has sustained a bone fracture or cartilage injury. Such kits may comprise a binding partner for TGFβrIII and/or CRTAC-1, one or more buffers or solutions for carrying out the assay, and instructions that indicate how to use the kit to detect the presence of or measure the level of TGFβrIII and/or CRTAC-1 in a blood sample and to determine whether the individual has sustained a bone fracture or cartilage injury.

DETAILED DESCRIPTION OF THE INVENTION

The invention is based on the discoveries that transforming growth factor beta receptor III (TGFβrIII) appears in the peripheral blood of human individuals that sustain a bone fracture and that elevated levels of cartilage acidic protein 1 (CRTAC-1) appear in the peripheral blood of human individuals that sustain cartilage injury. Neither TGFβrIII nor CRTAC-1 was previously known to be released to the peripheral circulation as the result of injury to bone or cartilage tissue. The detection of TGFβrIII and elevated levels of CRTAC-1 in the blood of an individual may provide an even more sensitive indication of bone fracture and cartilage injury, respectively, than traditional diagnostic methods such as X-rays and bone scans for bone fractures and magnetic resonance imaging (MRI) for cartilage injury. Accordingly, TGFβrIII and CRTAC-1 are useful as blood biomarkers for bone fracture and cartilage injury, respectively.

Methods described herein may also be used in assessing or monitoring injury to bone and cartilage in individuals who are incapable of effective communication to a healthcare professional. Such individual may include, but are not limited to, infants; speaking impaired individuals; stroke patients; and patients in an altered consciousness state (ACS), such as coma, near coma, persistent vegetative state, vegetative state, or minimally conscious state. Methods described herein may also find use in the forensic analysis of injuries.

The methods and compositions of the present invention are contemplated to be applied to the detection or measurement of either or both TGFβrIII or CRTAC-1 in a sample of blood and are understood to encompass the detection in whole blood or fractions thereof, such as plasma or serum. Particularly preferred is the use of blood plasma in the methods and compositions described herein.

The methods and compositions of the present invention are especially contemplated to benefit human subjects, but they are suitable for any mammalian subject that expresses a TGFβrIII or a CRTAC-1.

In order that the invention may be more fully understood, the follow terms are defined.

Unless indicated otherwise, when the terms "about" and "approximately" are used in combination with an amount, number, or value, then that combination describes the recited amount, number, or value alone as well as the amount, number, or value plus or minus 10% of that amount, number, or value. By way of example, the phrases "about 40%" and "approximately 40%" disclose both "40%" and "from 36% to 44%, inclusive".

A "binding partner" is any molecule, including any polypeptide, immunoglobulin, nucleic acid, or fragment thereof, which specifically binds a cognate binding partner (cognate ligand) at one or more sites. Examples of binding partner/cognate ligand pairs include antibody/antigen, receptor/ligand, biotin/streptavidin, and enzyme/substrate. A binding partner that is a polypeptide may also be referred to as a "binding protein". Binding partners useful in the methods and compositions described herein include antibody molecules specific for TGFβrIII or CRTAC-1. A binding partner that is a nucleic acid is referred to as an aptamer.

A "TGFβrIII binding partner" is any binding partner molecule, including any polypeptide, immunoglobulin, or fragment thereof, which specifically binds transforming growth factor beta receptor III (TGFβrIII) or an epitope thereof at one or more sites in the molecule.

A "CRTAC-1 binding partner" is any binding partner molecule, including any polypeptide, immunoglobulin, or fragment thereof, which specifically binds cartilage acidic protein 1 (CRTAC-1) or an epitope thereof at one or more sites in the molecule.

A "TGFβrIII antibody" refers to a binding protein that contains at least one antigen binding site that binds TGFβrIII or an epitope thereof. Similarly, a "CRTAC-1 antibody" refers to a binding protein that contains at least one antigen binding site that binds CRTAC-1 or an epitope thereof.

An "antibody" includes any of the classes of full-length mammalian immunoglobulin classes (such as IgG, IgM, IgA, IgE, IgD) and subclasses thereof. An "antibody" may also be any fragment of a full-length immunoglobulin that binds the same antigen, such a Fab, F(ab')$_2$, and Fv fragments, as well as binding molecules that may be produced by protein engineering or recombinant DNA technology, including but not limited to, a chimeric antibody, which comprises a binding domain or complementarity determining regions (CDRs) of an immunoglobulin fused or inserted into another immunoglobulin; a humanized antibody, which comprises the CDRs from a non-human antibody inserted into the framework of a human antibody molecule; a single chain antibody (scFv); and a diabody (see, e.g., Holliger et al., *Proc. Natl. Acad. Sci. USA*, 90: 6444-6448 (1993)).

An antibody useful in the methods and compositions described herein may be monovalent, i.e., having a single binding site for binding a single antigen (or epitope) molecule, or multivalent, i.e., having more than one binding sites for binding more than one antigen (or epitope). A classic IgG antibody molecule has two antigen binding sites and, thus, is bivalent.

An antibody useful in the methods and compositions described herein may be monospecific, i.e., binding a single type of antigen (or epitope), or multispecific, i.e., binding two or more different antigens (or epitopes). A classic IgG antibody molecule that has two identical antigen binding sites is thus monospecific with respect to the type of antigen (or epitope) that it can bind. A bispecific antibody binding partner useful in the invention can bind at least one molecule of TGFβrIII and at least one molecule of CRTAC-1. Bispecific antibody molecules may be heterodimers of two halves of two different full-length immunoglobulin molecules. For example, bispecific antibodies have been described using "quadroma" technology that fuses two different hybridoma cell lines, each capable of expressing a monoclonal antibody that binds a different antigen. Random pairing of light and heavy chains of the two monoclonal antibodies include heterodimers comprising a pair of heavy and light chains of one monoclonal antibody associated with a pair of heavy and light chains of the other monoclonal antibody (see, e.g., Milstein et al., *Nature,* 305: 537-540 (1983)). A variety of other bispecific antibody molecules have been described using protein engineering and recombinant DNA technology (see, e.g., Kriangkum et al., *Biomol. Eng.,* 18(2): 31-40 (2001)). Bispecific antibodies useful in the invention may include, but are not limited to, bispecific diabodies (e.g., Holliger et al. (1993); Holliger et al., *Cancer Immunol. Immunother.,* 45: 128-130 (1997); Wu et al., *Immunotech.,* 2(1): 21-36 (1996)), bispecific tandem scFv molecules, Fab mulitmers (see, e.g., Miller et al, *J. Immunol.,* 170: 4854-4861 (2003)), and dual variable domain immunoglobulins (see, e.g., Wu et al., *Nature Biotechnology,* (Oct. 14, 2007)).

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

It is also understood that an element or step "selected from the group consisting of" refers to one or more of the elements or steps in the list that follows, including combinations of any two or more of the listed elements or steps.

The meanings of other terms will be evident to those skilled in the art including the meanings known in fields of orthopedic medicine, molecular biology, immunology, and diagnostic methodologies.

Cartilage acidic protein 1 (CRTAC-1) is a glycosylated extracellular matrix protein that has been isolated from human articular cartilage secreted by chondrocytes. In cell culture, CRTAC-1 has been described as a candidate marker to distinguish the chondrocyte-like phenotype and activity from osteoblast-like and mesenchymal stem cells (Steck et al., *Matrix Biol.,* 26: 30-41 (2007)).

Transforming growth factor beta receptor III (TGFβrIII) is known to be involved in developmental and regenerative processes. For example, TGFβrIII plays an essential role in murine and chick development, and TGFβrIII knockout mice have an embryonic lethal phenotype. TGFβrIII functions as a co-receptor for TGF-β signal transduction by enhancing TGF-β binding to its receptor TGFβrII and thereby increasing TGF-β signaling (see, e.g., Massague, J., *Ann. Rev. Biochem.,* 67: 753-791 (1998)). Enhancement of TGF-β signaling is important in bone fracture healing wherein TGF-β1 and its receptor TGFβrII, together with extracellular matrix proteins osteocalcin and collagen type I, are involved in a coordinated manner to promote proper healing of bone fractures.

Transforming growth factor beta receptor III (TGFβrIII) and cartilage acidic protein 1 (CRTAC-1) have not previously been reported to be a component in the blood of humans. Both proteins were detected in plasma from human individuals that sustained long bone fractures (see, Example 1, below). Further analysis revealed that TGFβrIII is normally not found in the blood of healthy human individuals but is present in the blood of individuals who have sustained a bone fracture. In contrast, CRTAC-1 may be found in the blood of healthy individuals but will be present at elevated levels in the peripheral blood in an individual that has sustained a cartilage injury. Moreover, the level of both proteins in circulating blood show a similar pattern of change in the weeks following the injuries with which we have found them to be associated: the levels fluctuate between wide limits within the first ten weeks following injury, first increasing significantly and precipitously in the first 2 or 4 weeks (for TGFβrIII and CRTAC-1, respectively), then falling significantly over the next 6 weeks or so, then finally leveling off to essentially a steady state, neither increasing nor decreasing significantly for 14 weeks or longer. See FIGS. 1 and 2.

According to the invention, a level of CRTAC-1 in a blood sample from of an individual that is at least about 20% higher than a previously determined level of CRTAC-1 in a sample of blood from the individual (i.e., a baseline level) or at least about 20% higher than an estimated baseline level from healthy (non-injured) individuals or historical controls indicates that individual has sustained a cartilage injury.

According to the invention, a preferred method for detecting a bone fracture in a human individual comprises the steps of obtaining a sample of blood from the human individual and assaying the sample of blood for the presence of transforming growth factor beta receptor III (TGFβrIII), wherein the detection of TGFβrIII in the blood sample indicates that the individual has sustained a fracture in a bone.

Any fracture of bone stimulates the process of bone formation, i.e., osteogenesis, to regenerate bone and heal the fracture. Since TGFβrIII is known to play a role in enhancing TGF-β signal transduction in the process of bone formation (osteogenesis), the presence of TGFβrIII in a sample of blood obtained from an individual may also be used as an indication that osteogenesis has been stimulated in response to a fracture. Likewise, because CRTAC-1 is a component in the process of cartilage formation (chondrogenesis), the determination that the level of CRTAC-1 in the blood of an individual is elevated may be used as an indication that the process of chondrogenesis has been stimulated in response to a cartilage injury.

Fractures in bone as detected by a method described herein may result from any of a variety of conditions including, trauma and bone diseases. Metabolic bone diseases include, but are not limited to, osteoarthritis, osteoporosis, and osteogenesis imperfecta (OI, "brittle bone disease"). Fractures may occur in patients with osteoarthritis where a full thickness defect in a joint so depletes the articular cartilage that normally cushions two opposing bones that the two bones make contact and grind against one another and eventually fracture the surface of either or both of the opposing bones. Osteoporosis and OI are examples of bone diseases in which the bones of an individual are or can become unusually brittle and susceptible to fracture. For example, clinically undetected fractures, such as microfractures, can occur in trabeculi within vertebrae or in the proximal and distal metaphyseal areas of bones of individuals with osteoporosis. In the case of OI, bones can be so brittle that relatively minor trauma (bumps) cause fractures that would not normally occur in the bones of healthy individuals. Accordingly, testing a sample of peripheral blood for the presence of TGFβrIII as described herein may be advantageously used to routinely monitor for bone fracture in a variety of patients without the need of equipment and time involved in subjecting such patients to X-ray or bone scan procedures. Moreover, methods described herein may indicate fractures that cannot be detected using conventional X-rays and bone scans, such as microfractures and occluded fractures.

Figure 1:
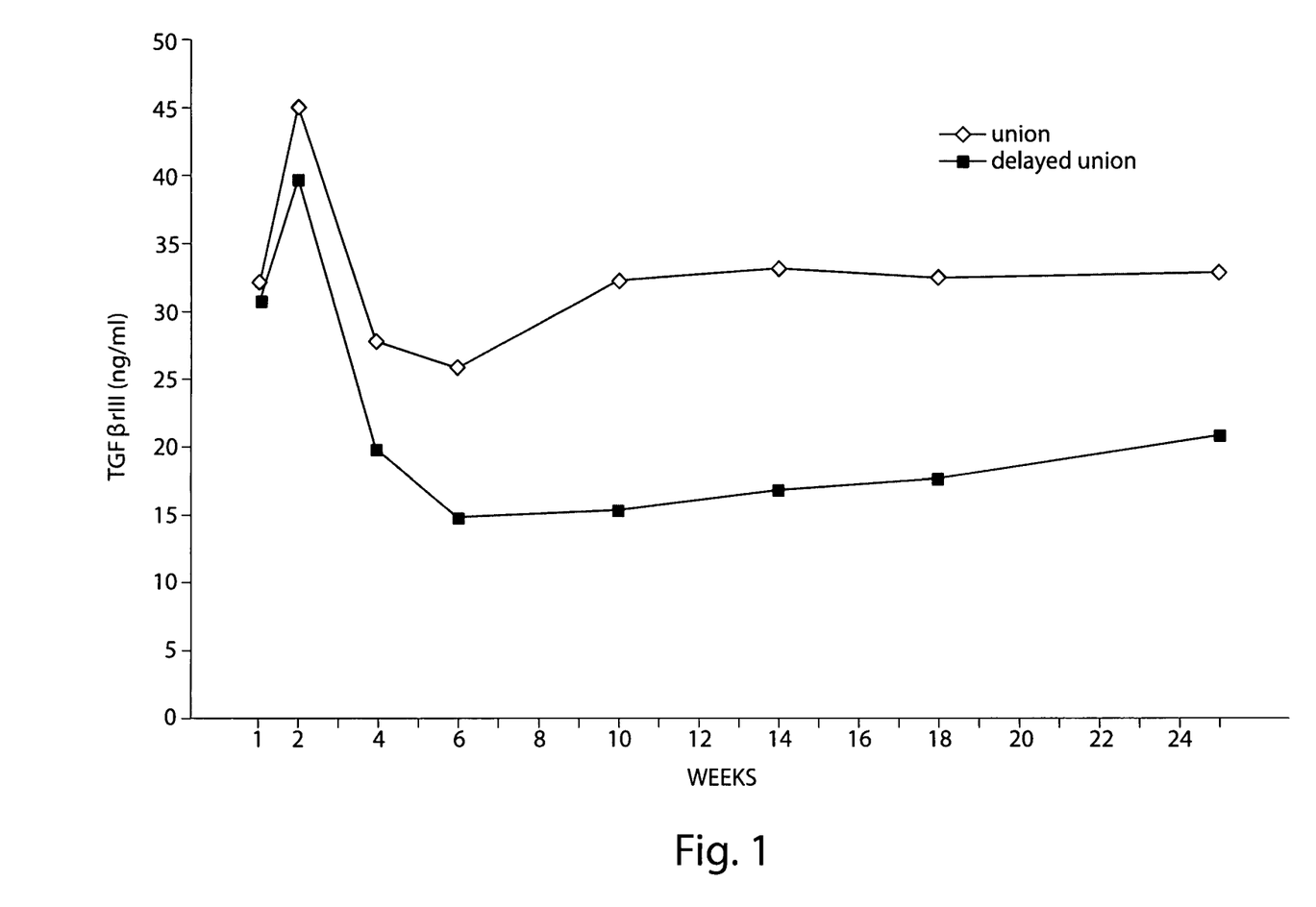
FIG. 1 shows graphs of the level (ng/ml) of transforming growth factor beta receptor III (TGFβrIII) in blood samples (plasma) from patients that sustained a single traumatic fracture in the tibia as determined with 24 hours of injury and continuing for 24 weeks after injury as described in Example 2, below. Diamonds indicate the average level of TGFβrIII in blood samples from patients (n=26) in which the bone fracture healed over the course of 24 weeks following injury ("union"). Squares indicate the average level of TGFβrIII in blood samples from patients (n=4) in which the fracture did not heal over the course of 24 weeks following injury ("delayed union"). See description, infra, for details.

As described herein (see, Example 2, infra), a study of human patients who have sustained a traumatic bone fracture has revealed that the relative level of transforming growth factor beta receptor III (TGFβrIII) in the blood of an individual over time provides useful information regarding not only whether a fracture has occurred but the state of bone fracture in an individual. Representative data are shown in the graphs of FIG. 1 in which the level of TGFβrIII as measured in blood samples from a population of bone fracture patients is followed over time. One of the graphs in FIG. 1 shows the level of TGFβrIII in blood samples from a portion of the patient population in which the bone fractures healed by 24 weeks from injury ("union"). The other graph in FIG. 1 shows the level of TGFβrIII in blood samples from the portion of the patient population in which the bone fractures did not heal by 24 weeks from injury ("delayed union"). The data in FIG. 1 indicate that following fracture, the level of TGFβrIII in blood follows a relatively steep rise within about 2 weeks following injury, followed by a relatively symmetrical steep decline within about a further 2 weeks, i.e., between about 2 weeks and about 4 weeks following fracture, followed by a slower rate of decline at about 4 weeks to about 6 weeks following fracture, and, thereafter, from about 6 weeks out to about 24 weeks following injury, there is an extended leveling off in the case of fracture healing or a gradual rise in the case of delayed union.

Thus, another aspect of the invention is a method for monitoring the state of a bone fracture in an individual comprising assaying for the level of transforming growth factor beta receptor III (TGFβrIII) in a first blood sample and in a second blood sample, wherein the second blood sample was obtained within two weeks, preferably within a week, inclusive, after the first blood sample from the individual, and comparing the level of TGFβrIII in the first blood sample with that of the second blood sample. Moreover, an analysis of the representative data provided in FIG. 1, permits a number of correlations to be made between the change in the level of TGFβrIII present in such a first (earlier obtained) blood sample and a second (later obtained) blood sample with respect to the state of bone fracture in the individual including, but not limited to:

an increase in the level of TGFβrIII of at least about 20% or more between the first blood sample and the second blood sample indicates that the individual has sustained a bone fracture that occurred within about 1 to about 2 weeks prior to the time of the second blood sample;

a decrease in the level of TGFβrIII of at least about 10% or more between the first blood sample and the second blood sample indicates that the individual has sustained a bone fracture that occurred within about 2 to about 6 weeks prior to the time of the second blood sample;

a change in the level of TGFβrIII of about 6% or less, including no (0%) increase or decrease, indicates that the individual has sustained a bone fracture and has sustained no new bone fracture within about 6 weeks to about 24 weeks prior to the time of the second blood sample.

Damage to cartilage may occur as the result of trauma or a progressive disease that affects the cartilage tissue in joints or other parts of the body. For example, fractures to the distal portion of the tibia can extend into the ankle joint and damage the cartilage layer on the surface of the calcanear bone and/or the distal tibial joint surface (see, Example 2, infra). Injuries to cartilage are typically detected by magnetic resonance imaging (MRI). Clearly, an MRI can be useful in both locating a site of cartilage injury and assessing the particular damage that has occurred in cartilage tissue. However, methods described herein for testing a blood sample for elevated levels of CRTAC-1 may be used to determine if an individual has sustained a cartilage injury without the use of an MRI.

Moreover, methods described herein can be used to determine whether an MRI study is even necessary. In particular, testing a sample of blood for an elevated level of expression of CRTAC-1 as described herein is a convenient means for determining whether a cartilage injury may even exist in an individual. Moreover, obtaining a blood sample to determine the level of CRTAC-1 as described herein may be significantly less stressful for some individuals than being subjected to the constraint, noise, time, and expense involved in conducting an MRI study, especially if the analysis of the blood sample indicates there is no cartilage injury so that an MRI procedure is unnecessary.

Methods described herein to determine whether an individual has sustained a cartilage injury may comprise the step of comparing a level of CRTAC-1 in a blood sample from the individual with a reference level or reference range of concentration of CRTAC-1 that is indicative of the level of CRTAC-1 present in the blood of healthy human individuals that do not have a cartilage injury. A reference level or reference concentration range of CRTAC-1 that is indicative of normal cartilage health may be obtained from a population of healthy individuals with normal healthy cartilage tissue. The use of reference levels or reference ranges of concentrations for a blood biomarker is the basis for virtually every biomarker currently used in blood tests to assess the health of human patients. Accordingly, persons skilled in the art of optimizing diagnostic blood testing for use with respect to human individuals are familiar with the procedures for gathering and qualifying reference levels or concentration ranges of a particular biomarker in the blood of a population of healthy individuals that would be indicative of normal health (e.g., cartilage health) and the levels of the biomarker that would indicate relevant injury, disease, or condition (e.g., cartilage injury).

Alternatively, a method described herein may compare a level of CRTAC-1 measured in a blood sample from an individual with one or more levels of CRTAC-1 measured in one or more other blood samples that were obtained from the same individual at a different point in time (earlier or later). For example, testing the blood of an individual on a routine basis to monitor the change in the level of CRTAC-1 present in the blood over time, such as during periodic check-ups with a healthcare professional, is one way to provide a baseline CRTAC-1 level for an individual. A pronounced increase in the level of CRTAC-1 from such a baseline level of CRTAC-1 indicates that the individual has sustained an injury to cartilage tissue. Preferably, such a database for an individual provides levels of CRTAC-1 in one or more prior blood samples that were obtained from the individual when the individual is considered (e.g., by a healthcare professional) to have healthy cartilage, i.e., to not have sustained a cartilage injury.

A comparative study of levels of CRTAC-1 in blood from human patients is described in Example 2 (infra). All patients in the study sustained a traumatic fracture in the tibia. A portion of the population of fracture patients sustained a single fracture in the middle shaft or in the distal portion of the tibia and no cartilage injury. Among these patients with a single fracture, a portion ("union") healed over the course of 24 weeks after the time of injury (traumatic event). The other portion ("delayed union") failed to heal over the same 24 week post trauma. Another group of patients ("cartilage damage") sustained a fracture in the distal portion of the tibia that extended into the ankle joint with a visible dislocation of the joint and damage to the cartilage layer on the surface of the calcanear bone and/or distal tibial joint surface and, thus, sustained a cartilage injury.

Figure 2:
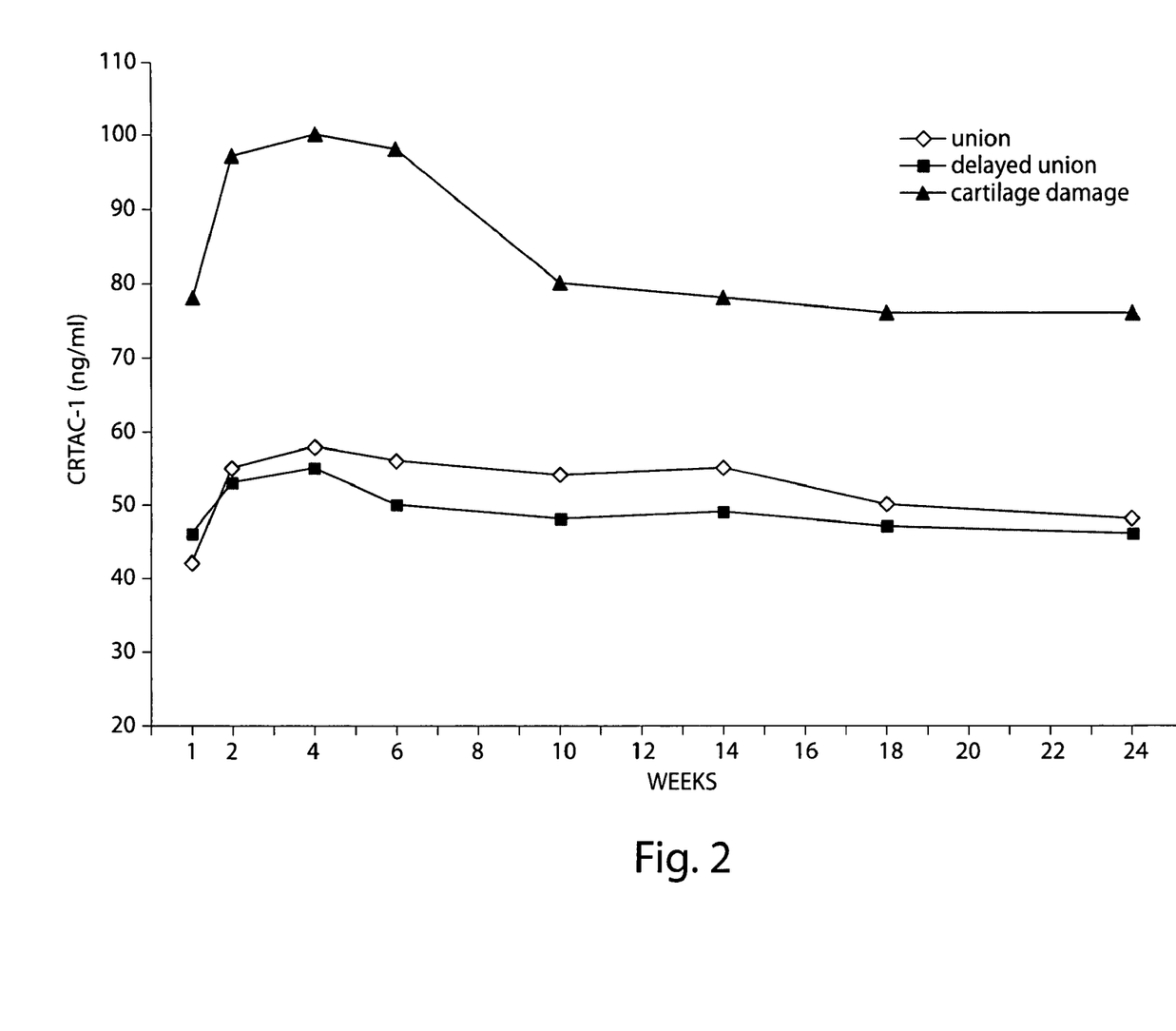
FIG. 2 shows graphs of the level (ng/ml) of cartilage acidic protein 1 (CRTAC-1) in blood samples (plasma) from patients that sustained a single fracture in the middle shaft or in the distal portion of the tibia without cartilage injury ("union", "delayed union") and in blood samples from patients that sustained a fracture in the middle shaft of the tibia and also a fracture in the distal portion extending into the ankle joint with visible dislocation of the joint and damage to the cartilage layer ("cartilage damage") as described in Example 2, below. Triangles indicate the average level of CRTAC-1 in blood samples from patients (n=8) that sustained bone fractures and cartilage damage as determined over the course of 24 weeks following injury ("cartilage damage"). Diamonds indicate the average level of CRTAC-1 in blood samples from patients (n=26) that sustained a bone fracture that healed over the course of the 24 weeks following injury ("union"). Squares indicate the average level of CRTAC-1 in blood samples from patients (n=4) that sustained a bone fracture that did not heal over the course of 24 weeks following injury ("delayed union"). See description, infra, for details.

FIG. 2 shows graphs of the levels of CRTAC-1 in blood of patients in the three groups in the comparative study over the course of 24 weeks from the time of injury. The levels of CRTAC-1 in blood from the patients with a single fracture and no cartilage damage ("union" and "delayed union") serve as a control for the background fracture in the patients with cartilage damage ("cartilage damage"). In the case of the "union" and "delayed union" groups in FIG. 2, the level of CRTAC-1 initially rose relatively steeply within about the first 2 weeks from the time of injury, followed by a period of more gradual rise for about another two weeks, i.e., at about 2 to about 4 weeks from injury, and thereafter, leveled off or gradually declined over the course of about 4 to about 24 weeks. In comparison, the level of CRTAC-1 in blood from the "cartilage damage" group rose relatively steeply over the first 2 weeks from time of injury, followed by a period of considerably slower increase or leveling off at about 2 to about 6 weeks from the time of injury, followed by a period of decline for about four weeks, i.e., at about 6 to about 10 weeks, and thereafter, gradually declined and leveled off over the course of about 10 weeks to about 24 weeks from time of injury until it reached the approximately same level or lower than first measured after injury.

FIG. 2, shows that throughout the 24 week study, the level of CRTAC-1 in patients with cartilage injury ("cartilage damage") was always at least about 40% higher than the level of CRTAC-1 in blood from patients without cartilage injury ("union", "delayed union"). Accordingly, in one aspect of the invention, a level of CRTAC-1 in a sample of blood from an individual indicates that the individual has sustained a cartilage injury when the level of CRTAC-1 is at least approximately 40% (including, in order of increasing preference, at least about 50%, at least about 60%, at least about 70%, at least about 80%, at least about 90%, and at least about 100%) higher than a level of CRTAC-1 previously determined in a sample of blood from the individual when the individual was known to have healthy cartilage or known to not have sustained a cartilage injury.

Another aspect of the invention is a method of monitoring the state of a cartilage injury in an individual comprising assaying for the level of cartilage acidic protein 1 (CRTAC-1) in a first blood sample and in a second blood sample, wherein the second blood sample was obtained from the individual within two weeks, preferably within a week, inclusive, of the first blood sample from the individual, and comparing the level of CRTAC-1 in the first blood sample with that in the second blood sample. Moreover, an analysis of the representative data provided in FIG. 2, permits a number of correlations to be made between the change in the level of CRTAC-1 present in such a first (earlier obtained) blood sample and a second (later obtained) blood sample with respect to the state of cartilage injury in the individual including, but not limited to:

an increase in the level of CRTAC-1 of at least about 20% or more (more preferably at least about 24% or more), between the first blood sample and the second blood sample indicates that the individual has sustained a cartilage injury that occurred within about 1 to about 2 weeks prior to the time of the second blood sample;

a decrease in the level of CRTAC-1 of about 4.5% or more between the first blood sample and the second blood sample indicates that the individual has sustained a cartilage injury that occurred within about 6 to about 10 weeks prior to the time of the second blood sample;

a change (increase or decrease) in the level of CRTAC-1 of less than 2% between the first blood sample and the second blood sample indicates that the individual is in a steady state and has sustained no new cartilage injury for at least about 10 weeks prior to the time of the second blood sample.

The accuracy of correlating a level or a difference in level of TGFβrIII or CRTAC-1 biomarkers in one or more blood samples obtained from an individual with the presence of a bone fracture or cartilage injury or with the state of bone fracture or cartilage injury in the individual will improve to the extent that the assays used to measure levels of TGFβrIII or CRTAC-1 biomarkers in blood samples are exactly repeated or comparably as accurate as those used to produce the data in Example 2 (infra) and FIG. 1 (for TGFβrIII) and FIG. 2 (for CRTAC-1). Furthermore, it will be obvious to practitioners that when monitoring the level of TGFβrIII or CRTAC-1 biomarkers for determining the stage of recovery from a bone or cartilage injury that the frequency of measurements will have an impact on the accuracy of the method, i.e., with more frequent blood samples taken closer together increasing the ability to correctly determine the stage of an injury in a patient or the proximity to an injury event. Yet practitioners will also recognize that measurements of TGFβrIII and CRTAC-1 biomarkers in blood samples that are taken over an extremely short period of time may undercut the accuracy or significance of the methods described herein. Therefore, a sufficient period of time must pass between time points at which blood samples are taken to permit the detection of a change in the level of a biomarker to become evident. Preferably, blood samples employed in methods described herein are not taken more frequently than one per day.

Any of a variety of means for the detection of TGFβrIII and/or CRTAC-1 in a sample of blood may be employed in the methods and compositions described herein, including detection using liquid chromatography and mass spectrometry. TGFβrIII or CRTAC-1 may also be detected in a sample of blood from an individual by contacting the blood sample with a binding partner for TGFβrIII or a binding partner for CRTAC-1. Most preferably, a binding partner used to detect TGFβrIII or CRTAC-1 is an antibody molecule. Antibodies may be obtained commercially or generated by various methods known in the art. An antibody may be a polyclonal antibody, a monoclonal antibody, or a recombinant antibody molecule.

The use of an antibody molecules as the binding partner to detect TGFβrIII or CRTAC-1 is particularly advantageous as antibodies may be employed in various formats and protocols known in the art for the detection (immunodetection) and measurement (quantitation) of a target antigen (TGFβrIII or CRTAC-1) in a sample. Such formats and protocols for the immunodetection or quantitation of TGFβrIII or CRTAC-1 in a sample of blood may include, without limitation, enzyme linked immunoadsorbent assays (ELISAs), immunoblots (e.g., Western blots), immunoprecipitations, immunoaffinity chromatography, and dip sticks. In such formats and protocols, antibodies may be immobilized on the surface of a solid substrate, e.g., by adsorbing or linking the antibodies to the surface of the substrate. Examples of immobilized antibodies on the surface of a solid substrate may take any of a variety of forms known in the art including, but not limited to, the surface of a magnetic or chromatographic matrix particle, the surface of the wells of a microtiter assay plate, and the surface of pieces or sheets of a solid substrate material (e.g., plastic, nylon, wood, cellulose, nitrocellulose, cellulose acetate, glass, cotton, fiberglass, and the like). Pieces of solid substrate material containing immobilized antibody adsorbed may be used as assay strips (or dipsticks) that can be dipped into or otherwise brought into contact with a blood sample either manually or robotically and then removed to detect the presence of bound antigen.

Protocols in which an antibody or other binding partner are adsorbed or linked to the surface of a substrate preferably include the pretreatment of the antibody containing substrate with a protein mixture (e.g., gelatin, bovine serum albumin, and the like) to block undesired non-specific binding of molecules to the surface of the substrate.

An immunocomplex formed by the binding of an antibody to its cognate antigen may be directly detected by the presence of a detectable label or tag molecule attached to the antibody or indirectly detected by the use of another molecule, such as another antibody, which can in turn be detected. Detectable labels for use with antibodies are well known in the art and include, but are not limited to, fluorescent labels, radioactive labels, biotin and streptavidin (or avidin) based detection systems, bioluminescent labels, chemiluminescent labels, and enzymes linked to an antibody that are capable of reacting with colorigenic substrates to produce a detectable signal. A signal generated by such systems may be readily detected visually or by an appropriate instrument and in some cases quantified, e.g., by fluorimetry, epifluorescence microscopy, confocal scanning laser microscopy, a luminometer, or a colorimetric assay. Robotic instruments are also available that permit the reading of multiple samples with minimal human intervention.

A sandwich assay is a type of indirect assay for an immunocomplex. A sandwich assay may use a first antibody (the capture antibody) that will bind to its cognate target antigen (e.g., TGFβrIII or CRTAC-1) in a sample to form an immunocomplex. The sample containing the capture antibody may then be reacted with a second antibody molecule (the detection antibody) that can bind to an epitope on the capture antibody or to an epitope that may be available on the antigen in the immunocomplex. The detection antibody may carry a detectable label or component of a signal generation system available in the art. By way of example and without intending to limit the invention, a capture antibody may be a murine IgG antibody to TGFβrIII or CRTAC-1, and the detection antibody may be a goat anti-murine IgG antibody that is conjugated to a detectable fluorescent tag molecule.

The invention further contemplates a method for detecting or measuring the level of TGFβrIII and the level of CRTAC-1 in peripheral blood of a human individual comprising the steps of obtaining a sample of peripheral blood from the individual and assaying the sample of blood for the level of TGFβrIII and CRTAC-1. Preferably, the level TGFβrIII and CRTAC-1 in the blood sample is determined by contacting the blood sample with a binding partner for TGFβrIII and a binding partner for CRTAC-1. Depending on the format of the assay, the blood sample may be brought into contact with each binding partner separately (i.e., in separate assays), consecutively in the same assay, or simultaneously in the same assay.

Materials necessary for detection of TGFβrIII or CRTAC-1 in a sample of blood (or plasma or serum) are conveniently assembled into a kit, so that personnel treating or transporting a trauma victim can determine quickly whether a bone fracture has been sustained by a patient. A preferred kit of the invention comprises a first (capture) binding partner(s) for either or each of TGFβrIII or CRTAC-1 immobilized on a solid substrate material, such as an anti-TGFβrIII or anti-CRTAC-1 antibody immobilized on an assay strip, the wells of a microtiter plate, or on beads or particles; a second (capture) binding partner that will bind the first binding partner and that contains a detectable label or component to produce a detectable signal; and instructions that indicate how to use the kit to carry out the assay to detect either or both TGFβrIII and CRTAC-1 in a peripheral blood sample. Beads, assay strips, or microtiter plates containing immobilized first binding partner molecules in kits of the invention may be packaged in a variety conditions, including a dry, unhydrated state; a freeze-dried or dehydrated state; or a hydrated state in a physiological buffer solution. Kits may also contain a device for obtaining a sample of blood from an individual (e.g., a syringe or small pin to obtain a few drops of blood). Kits may also contain other solutions for washing, for blocking non-specific binding, or for signal generation may also be included in the kits of the invention. In a preferred embodiment, a kit of the invention comprises capture binding partner(s) immobilized on a solid substrate, such as a bead, an assay strip or a microtiter plate, which has also been pretreated to prevent interference by non-specific binding of molecules to the substrate.

The methods and compositions described herein may find use in rapid diagnosis for bone or cartilage injury by emergency and medical personnel or in the periodic monitoring of the condition of a bone fracture or cartilage injury. The nature of the methods and compositions described herein makes it possible to perform diagnosis and monitoring of bone and cartilage injuries in a variety of environments, including ambulances or other mobile medical facilities, laboratories, hospitals, emergency rooms, sanitoria, homes, and other private facilities.

Additional embodiments and features of the invention will be apparent from the following non-limiting examples.

EXAMPLES

Example 1

Identification of Candidate Protein Biomarkers for Bone and Cartilage Metabolism in Plasma from Human Patients with Long Bone Fractures In this study, samples of blood were drawn from human patients with an acute bone fracture and analyzed for expression of candidate biomarkers for bone fracture and fracture healing. The plasma proteins of patients were characterized by sodium dodecyl sulfate polyacrylamide gel electrophoresis (SDS-PAGE) and affinity purification, followed by tandem mass spectrometry liquid chromatography (LC-MS/MS). LC-MS/MS provides picomolar level of detection of proteins expressed in the plasma samples. Following identification of proteins expressed in the plasma of the fracture patients, those species that are associated with bone and cartilage metabolism were singled out for further analysis.

Materials and Methods
Plasma Collection

Human blood plasma samples were supplied by the Clinic of Traumatology in Zagreb, Croatia. The approval for the collecting samples was obtained from the Ethics Committee of the same institution. Blood samples from 25 adult humans with a single long bone fracture (21-60 years of age) were drawn into syringes containing 3.8% sodium citrate to form an anticoagulant-to-blood ratio (v/v) 1:9. Plasma was obtained by centrifugation (15 min at 3000×g), and aliquots of each adult blood sample were pooled for the further analysis. Aliquot samples were stored at −80° C. until used.

Affinity Column Purification

Pooled plasma of patients with a single-bone fracture (80 ml) was diluted two-fold with 10 mM sodium phosphate buffer (pH 7), and applied to a column of heparin Sepharose affinity chromatography matrix (Amersham Pharmacia Biotech), previously equilibrated with 10 mM sodium phosphate buffer (pH 7). Bound proteins were eluted from the column with 10 mM sodium phosphate buffer (pH 7) containing 1 M and 2 M NaCl. Eluted fractions were precipitated with saturated ammonium sulfate (SAS) to final concentration of 35%.

SDS-PAGE and In-Gel Digestion

Samples were run on a NUPAGE® 10% Bis-Tris SDS-PAGE system (Invitrogen, Carlsbad, Calif.) using MOPS SDS buffer system, and subsequently stained with Coomassie staining kit (NuPAGE, Invitrogen) following manufacturer's instructions. After staining, each of the seven gel lanes was sliced into 12 pieces, and the corresponding pieces were combined. The pieces were then subjected to in-gel reduction, alkylation, and trypsin digestion as described previously (Grgurevic et al., *J. Nephrol.*, 20: 311-319 (2007)). Gel pieces were washed two times with acetonitrile/25 mM $NH_4HCO_3$, reduced by incubation with 10 mM dithiothreitol (DTT) for 45 minutes at 56° C., and carboxyamidomethylated by incubation in 55 mM iodoacetamide for 45 minutes at room temperature. Trypsin (Promega) was added to dried gel pieces (150 ng per piece, diluted in 25 mM $NH_4HCO_3$) and incubated overnight at 37° C. Tryptic peptides were extracted with formic acid/acetonitrile/$H_2O$ (10:20:70); and 100% acetonitrile, dried and resuspended in trifluoroacetic acid/acetonitrile/$H_2O$ (1:2:97) for MS analysis.

Mass Spectrometry

Tryptic peptides were analyzed by liquid chromatography-mass spectrometry (LC-MS). An Agilent 1100 nanoflow HPLC system (Agilent Technologies) was coupled to a LTQ-Orbitrap mass spectrometer (Thermo Scientific) using a nano-electrospray LC-MS interface (Proxeon Biosystems). Peptides were loaded on a home-made 75 μm $C_{18}$ HPLC column in solvent "A" (0.5% acetic acid in Milli-Q water) and eluted with a 70-minute segmented linear gradient of 10%-60% solvent "B" (80% acetonitrile, 0.5% acetic acid in Milli-Q water) at a flow rate of ca. 250 mL/min. Mass spectrometer was operated in the positive ion mode. Each measurement cycle consisted of a full MS scan acquired in the orbitrap analyzer at a resolution of 60000, and MS/MS fragmentation of the five most-intense ions in the linear ion trap analyzer. To further improve mass accuracy, the lock-mass option was used as described previously (Olsen et al., *Mol. Cell. Proteomics*, 4: 2010-2021 (2005)). This resulted in a typical peptide average absolute mass accuracy of less than 1 ppm.

Peak lists were generated using in-house developed software (Raw2 msm) (Olsen et al., 2005), and searched against concatenated forward and reverse ("decoy") IPI human database (version 3.13) using Mascot search engine (Matrix Science). Searches were done with trypsin specificity (2 missed cleavages allowed), carboxyamidomethylation as fixed modification, and oxidized methionine as variable modification. Precursor ion and fragment ion mass tolerances were 10 ppm and 0.5 Da, respectively. Results of the database search were validated in the MSQuant software (available from SOURECEFORGE.NET®). Only peptides with a mass deviation lower than 5 ppm were accepted; two peptides were required for protein identification. Gene ontology (GO) analysis was performed using ProteinCenter software package (Proxeon Biosystems).

Results

Pooled plasma samples were subjected to heparin affinity chromatography to enrich for proteins specific for bone and cartilage, many of which are known to have heparin binding domains. This also partially removed highly abundant plasma proteins, such as albumin, immunoglobulins, transferin, and haptoglobulin. Fractions of interest were collected, precipitated, with ammonium sulfate and separated on one dimensional SDS-PAGE gels. Gel bands were excised, digested with trypsin, and analyzed by LC-MS/MS. Peptide fragmentation spectra were searched against the human IPI protein database, and the results of the database search were validated using MSQuant software. Only peptides with a mass deviation lower than 5 ppm were accepted; two peptides were required for protein identification, which led to an overall false-positive rate of less than 1% at both the peptide and the protein level.

In total, two hundred and thirteen nonredundant proteins were identified in the in-gel analysis of pooled plasma proteins from 25 patients with a bone fracture. Gene ontology (GO) analysis of plasma proteins showed that a majority (63.8%) of detected proteins were of extracellular origin, whereas only a small number (7.5%) were of intracellular (cytosol and nucleus) origin. Interestingly, a relatively high number (35.2%) of membrane related proteins were also detected.

According to molecular function analysis, 37.6% of detected proteins had catalytic properties, 18.3% were classified as signal transducers, and 13.1% as transporters.

In terms of biological activity, a significant proportion of detected proteins were involved in cell growth and proliferation (21.1%), transport (23.9%) and coagulation (13.1%).

Identification of Bone- and Cartilage-Related Proteins

From the proteins initially identified by the methodology described above in the pooled plasma samples of individuals with a long bone fracture, the twelve proteins listed in Table 1, below, were considered as having possible involvement in bone and cartilage metabolism.

TABLE 1

Proteins in Plasma of Bone Fracture Patients Related to Bone and Cartilage Formation

| Protein | IPI Accession No. | GO console: Molecular Function | Previously Identified in Plasma |
|---|---|---|---|
| transforming growth factor beta receptor III (TGFβrIII) | 304865.3 | receptor activity signal transducer | No |
| splice isoform 1 of cartilage acidic protein 1 precursor (CRTAC-1) | 451624.1 | metal ion binding | No |
| extracellular matrix protein 1 precursor | 3351.2 | signal transducer structural molecule transporter activity | Yes |

TABLE 1-continued

Proteins in Plasma of Bone Fracture Patients
Related to Bone and Cartilage Formation

| Protein | IPI Accession No. | GO console: Molecular Function | Previously Identified in Plasma |
|---|---|---|---|
| transforming growth factor beta induced protein IG-H3 precursor (TGFβ IG-H3) | 18219.1 | protein binding | No |
| splice isoform 2 of collagen alpha 3 (VI) chain precursor | 220701.3 | enzyme regulator activity protein binding structural molecule | Yes |
| type IV collagenase precursor | 27780.1 | catalytic activity enzyme regulator activity metal ion binding | Yes |
| alpha 3 type VI collagen isoform 1 precursor | 22200.2 | enzyme regulator activity protein binding structural molecule | No |
| procollagen C proteinase enhancer protein precursor | 299738.1 | nucleic acid binding protein binding | No |
| isoform long of collagen alpha-1 (XVIII) chain precursor | 22822.4 | metal ion binding protein binding structural molecule | Yes |
| hyaluron binding protein 2 precursor | 41065.3 | catalytic activity | Yes |
| metalloproteinase inhibitor 1 precursor | 32292.1 | catalytic activity enzyme regulator metal ion binding | Yes |
| splice isoform A of proteoglycan-4 precursor | 24825.2 | not known | Yes |

As noted in Table 1, above, among the twelve proteins considered to be involved in bone and cartilage metabolism, five were not previously identified in plasma.

Cartilage acidic protein 1 (CRTAC-1) was identified for the first time in plasma with 28 peptides and an average peptide Mascot score of 53.

Transforming growth factor beta receptor III (TGFβrIII) was identified for the first time in plasma with four specific peptides and an average Mascot score of 44.

Transforming growth factor beta induced protein IG-H3 (TGFβ-IG-H3) was also identified for the first time in plasma with 20 peptides and an average peptide Mascot score of 57.

Among extracellular matrix proteins which were not previously detected in plasma was the alpha 3 type VI collagen isoform 1 identified with two peptides and an average peptide Mascot score of 60.

Previously identified in plasma, the splice isoform A of the proteoglycan-4 (or lubricin) was identified with two peptides and an average peptide Mascot score of 60.

Extracellular matrix proteins previously identified in plasma included: isoform long of collagen alpha-1 (XVIII) chain precursor (or endostatin) identified with five peptides and an average Mascot score of 36, splice isoform 2 of collagen alpha 3 (VI) chain precursor identified with ten peptides and an average Mascot score of 62, extracellular matrix protein 1 precursor identified with 57 peptides and an average Mascot score of 54, and type IV collagenase precursor (or matrix metalloproteinase-2, MMP2) identified with three peptides and an average Mascot score of 74. MMP-2 degrades extra-cellular proteins and disrupts the subendothelial basement membrane, thus enabling the transmigration of inflammatory cells. Metalloproteinase inhibitor 1 precursor (TIMP-1) was identified with five peptides and an average peptide Mascot score of 49. Example 2. Monitoring plasma levels of transforming growth factor β Receptor III (TGFβrIII) as blood biomarker for bone fracture and cartilage acidic protein 1 (CRTAC-1) as blood biomarker for cartilage injury.

In this study, the blood of human patients who sustained an acute bone fracture was monitored for the presence of transforming growth factor 13 receptor III (TGFβrIII) and cartilage acidic protein 1 (CRTAC-1).

Material and Methods

Patients

Within 24 hours of injury, thirty (30) patients (24-67 years of age) who sustained a fracture of the tibia were enlisted in this study. All patients gave written informed consent, and the study procedures were in accordance with the Ethics Committee of Clinics of Traumatology of the Medical School of Zagreb. The criterion for inclusion in the study was that a patient had a radiologically confirmed fracture in the middle shaft or in the distal portion of the tibia. An additional eight (8) patients had a fracture in the distal portion of the tibia that extended into the ankle joint with a visible dislocation of the joint and damage to the cartilage layer on the surface of the calcanear bone and/or distal tibial joint surface as diagnosed by magnetic resonance imaging (MRI).

Venous Blood Samples

From all included patients, peripheral venous blood was drawn at periodic intervals according to a standardized time pattern at day 1, 3, and 7 following injury, and then at 2, 6, 10, 14, 18, and 24 weeks following fracture. If the fracture healing was delayed, the blood samples were collected periodically until bony consolidation was achieved. Blood was drawn into syringes containing 3.8% sodium citrate to form an anticoagulant-to-blood ratio (v/v) 1:9. Plasma was obtained by centrifugation (15 min at 3 000×g), and aliquots of plasma samples were stored at −80° C. until used.

Radiological Evaluation

Physical examinations and radiographs were completed to assess the evidence of a bone union. At 24 weeks after injury, fractures were pronounced as healed or as non-union by two independent radiologists. All patients underwent surgery to insert an interlocking nail into the fracture. X-rays were taken pre-operatively, immediately postoperatively, and then at regular bi-weekly intervals up to 24 weeks following surgery. X-rays were taken in two positions, i.e., an anterio-posterior view and a latero-lateral view. A fracture was pronounced as healed when all four cortices healed. However, partial healing was graded when one, two, or three cortices rebridged. Additional injury of the calcanear or distal tibial joint cartilage was confirmed by MRI.

Measurement of TGFβrIII and CRTAC-1 in Blood Plasma

An enzyme-linked immunoadsorbent assay (ELISA) was developed to measure blood concentrations of TGFβrIII and CRTAC-1 in plasma from patient throughout the follow-up (24 week) period. Polyclonal antibodies were raised in rabbits immunized with specific human peptides of TGFβrIII and CRTAC-1 by standard methods. A monoclonal antibody against TGFβrIII was purchased from Santa Cruz (A-4: sc-74511-mouse monoclonal antibody). All samples from 30 patients were measured twice, and a mean value was then included in the final median range.

The ELISA for TGFβrIII specifically detects the biologically active soluble form of the TGFβrIII in human plasma with a sensitivity of 10 pg/ml. The minimal detectable dose of TGFβrIII ranged from 5.5 to 35 pg/ml.

The ELISA for CRTAC-1 in human plasma provided measurable levels of CRTAC-1 within a range of 10.5 to 55 pg/ml.

Formation of Cross-Linked Antibody-Protein G Complex and Immunoprecipitation

Rabbit polycloncal antibody (Genera Research Laboratory) against the soluble form of TGFβrIII or against CRTAC-1 was incubated with protein G agarose beads for 15 minutes on a shaker. The antibody-protein G bead samples were centrifuged for 2 minutes on 12,000×g, and the supernatants removed. Formalin (500 μl of 4% formalin) was then added to the pellet and incubated for another 30 minutes on the shaker. The samples were centrifuged for 2 minutes on 12,000×g, and the supernatants removed. The resulting pellets (antibody cross-linked to protein G beads) were resuspended in a phosphate-buffered saline (PBS) and added to collected plasma samples for immunoprecipitation of cognate antigen, i.e., TGFβrIII or CRTAC-1.

The mixtures of plasma samples and antibody cross-linked beads were incubated overnight to allow formation of immunocomplexes between antigen (TGFβrIII or CRTAC-1) in the plasma samples and the antibody cross-linked beads. The samples were then centrifuged for 2 minutes on 12,000×g to obtain pellets comprising immunocomplexes formed between TGFβrIII or CRTAC-1 and antibody cross-linked beads. The supernatants were removed, and the pellets were washed three times with a phosphate-buffered saline and prepared for gel electrophoresis.

Gel Electrophoresis and Western Immunobloting

Aliquots of samples were analyzed by electrophoresis and immunoblotting in a Novex mini-gel electrophoresis system. Gel electrophoresis sample buffer was added to each pellet. The samples were denatured by heating at 99° C. for 3 minutes followed by centrifugation for 2 minutes on 12,000×g. Supernatants were then analyzed on a 10% polyacrylamide/SDS gel (Invitrogen). After electrophoresis, proteins in the gels were transferred by electroblotting to nitrocellulose membranes and incubated first with rabbit antibody against TGFβrIII and rabbit antibody against CRTAC-1. The bound antibodies were detected with alkaline phosphatase-conjugated anti-rabbit IgG immunoglobulin (immunodetection kit, Invitrogen).

Results

Physical examinations and radiographs were completed to assess the evidence of a bone union in patients. At 24 weeks after injury, 26 fractures were pronounced as healed by two independent radiologists, while four (4) patients had non-union fractures. Six patients had an additional injury of the joint cartilage based on MRI analysis.

Reference Values

The postoperative TGFβrIII reference level in plasma of patients with normal fracture healing was 30.6±7.5 ng/ml (15-47 ng/ml). The level of TGFβrIII in plasma of patients with delayed union was 32.4±8.2 ng/ml (18-52 ng/ml) without a significant difference (P=0.861).

The plasma concentration of CRTAC-1 in patients with normal fracture healing was in the range of 50.4±9.1 ng/ml. In patients with a delayed union fracture, the value was 51.2±5.3 ng/ml. Plasma concentrations of CRTAC-1 in patients with an additional joint cartilage injury was 83.4±7.8 ng/ml (67-112 ng/ml), which was significantly higher than in patients without a joint cartilage injury (P<0.01, Wilcoxon test).

Time Courses

Levels of transforming growth factor β receptor III (TGFβrIII) in plasma of patients with a bone fracture that healed ("union") and in plasma of patients with a bone fracture that did not heal ("delayed union") over the course of 24 weeks following injury are shown in Table 2, below.

TABLE 2

Plasma Levels of TGFβrIII in Patients with Bone Fracture

| Week After Injury | TGFβrIII (union*, ng/ml) | TGFβrIII (delayed union‡, ng/ml) |
|---|---|---|
| 1 | 32.3 | 31 |
| 2 | 45.4 | 40 |
| 4 | 28 | 20 |
| 6 | 26 | 15 |
| 10 | 32.5 | 15.5 |
| 14 | 33.4 | 17 |
| 18 | 32.7 | 17.8 |
| 24 | 33.1 | 21 |

*"union" refers to patients with a bone fracture that healed within 24 weeks of injury;
‡"delayed union" refers to patients with a bone fracture that did not heal within 24 weeks of injury As can be seen from a graph of the data in Table 2 (FIG. 1), in patients with normal bone fracture healing ("union") as well as in patients with delayed bone fracture healing ("delayed union"), TGFβrIII plasma concentrations reached their highest values at week 2 following injury. After the second week, TGFβrIII plasma levels declined in patients with delayed union, and at 5 weeks following injury, TGFβrIII concentrations were below the reference level of this group of patients. In patients with a normal fracture healing ("union" in FIG. 1), TGFβrIII plasma concentrations also decreased after the second week following injury. However, the plasma value did not fall below the reference level, and slightly increased at 10 weeks following injury. Thereafter, the level did not change towards the end of the follow up period. See, FIG. 1. These data indicate that TGFβrIII is particularly useful as a blood biomarker for detecting bone fracture. With respect to the quantitative levels of TGFβrIII in the blood samples of the patients, the data in FIG. 1 indicate that if the level of TGFβrIII falls below 20 ng/ml after week 4, then there is a possibility that a delayed union or non-union fracture has developed. The data in FIG. 1 also indicate that the maintenance of blood levels of TGFβrIII above 25 ng/ml after week 4 reflects a normal healing process as confirmed by X-rays and clinical exam and a high probability that the bone will fully regenerate by week 24.

Table 3, below, shows the levels of cartilage acidic protein 1 (CRTAC-1) in plasma of patients with a bone fracture that healed ("union"), in plasma of patients with a bone fracture that did not heal ("delayed union"), and in plasma of patients that sustained a bone fracture and an articular cartilage injury ("cartilage damage") over the course of 24 weeks following injury.

TABLE 3

Plasma Levels of CRTAC-1 in Patients with Bone Fractures and Cartilage Injuries

| Week After Injury | Plasma CRTAC-1 (union*, ng/ml) | Plasma CRTAC-1 (delayed union‡, ng/ml) | CRTAC-1 (cartilage damage†, ng/ml) |
|---|---|---|---|
| 1 | 42 | 46 | 78 |
| 2 | 55 | 53 | 97 |
| 4 | 58 | 55 | 100 |
| 6 | 56 | 50 | 98 |
| 10 | 54 | 48 | 80 |
| 14 | 55 | 49 | 78 |
| 18 | 50 | 47 | 76 |
| 24 | 48 | 46 | 76 |

*"union" refers to patients with bone fracture that healed within 24 weeks of injury;
‡"delayed union" refers to patients with bone fracture did not heal within 24 weeks of injury;
†"cartilage damage" refers to patients that sustained bone fracture and cartilage injury As can be seen from a graph of the data in Table 3 (FIG. 2), in patients that sustained a bone fracture and also damage to articular cartilage ("cartilage damage"), the concentration of CRTAC-1 in the blood rose within a week of injury and persisted at a level that was clearly higher than the level of CRTAC-1 in the blood of patients that sustained a bone fracture without articular cartilage damage, whether the fracture healed ("union") or did not heal ("delayed union") within 24 weeks following injury. These data indicate that CRTAC-1 is useful as a blood biomarker for cartilage injury.

All publications, patent applications, patents, and other documents cited herein are incorporated by reference in their entirety. In case of conflict, the present specification, including definitions, will control. In addition, the materials, methods, and examples are illustrative only and not intended to be limiting.

Other variations and embodiments of the invention described herein will now be apparent to those skilled in the art, and all such variants and alternative embodiments of the invention are intended to be encompassed within the foregoing description and the claims that follow.

What is claimed is:

1. A method of determining whether a human individual has sustained a bone fracture comprising obtaining a blood sample from said individual and assaying said blood sample for the presence of transforming growth factor beta receptor III (TGFβrIII), wherein the presence of TGFβrIII in said blood sample indicates that said individual has sustained a bone fracture.

2. The method according to claim 1, wherein the step of assaying the blood sample for the presence of TGFβrIII comprises contacting the blood sample with a binding partner for TGFβrIII to form a binding complex between the binding partner and TGFβrIII present in the blood sample.

3. The method according to claim 2, wherein the binding complex formed between the binding partner and TGFβrIII present in the blood sample is detected by a detectable label present on the binding partner.

4. The method according to claim 2, wherein the binding complex formed between the binding partner and TGFβrIII present in the blood sample is detected by adding an antibody that binds to said binding partner or that binds to said TGFβrIII present in said binding complex and detecting said antibody by a detectable label present on said antibody.

5. The method according to any one of claims 1-4, wherein the binding partner for TGFβrIII is a binding protein or an aptamer that binds TGFβrIII.

6. The method according to claim 5, wherein said binding protein for TGFβrIII is an antibody that binds TGFβrIII.

7. A method of monitoring the state of a bone fracture in an individual comprising measuring the level of transforming growth factor beta receptor III (TGFβrIII) in a first blood sample obtained from the individual and comparing the level of TGFβrIII in the first blood sample with the level of TGFβrIII measured in a second blood sample, wherein the second blood sample was obtained within two weeks, inclusive, after the first blood sample from the individual, and determining whether the level of TGFβrIII in the second blood sample has increased, decreased, or remained the same relative to the level in the first blood sample.

8. A method for determining the time proximity of an individual from a bone fracture comprising:
   (a) obtaining a blood sample from said individual at a first time point,
   (b) obtaining at least one additional blood sample from said individual at a later time point,
   (c) determining the concentration of transforming growth factor beta receptor III (TGFβrIII) in at least said first blood sample and said at least one additional blood sample,
   wherein said first time point and said later time point are within two weeks of each other,
   wherein a determination that an increase in TGFβrIII concentration of at least about 20% has occurred between said first time point and said later time point indicates that the individual has suffered a bone fracture within two weeks prior to said later time point,
   wherein a determination that a decrease in TGFβrIII concentration of at least about 10% has occurred between said first time point and said later time point indicates that the individual has suffered a bone fracture more than two weeks but less than six weeks prior to said later time point, and
   wherein a determination that the concentration of TGFβrIII has neither increased nor decreased more than about 6% between said first time point and said later time point indicates that the individual has not suffered a bone fracture for at least six weeks since the later time point.

9. The method according to claim 8, wherein said first time point and said later time point are within one week of each other.

* * * * *